United States Patent [19]

Klausener et al.

[11] Patent Number: 5,008,275
[45] Date of Patent: Apr. 16, 1991

[54] PESTICIDAL PYRIDYL-SUBSTITUTED ACRYLIC ESTER COMPOUNDS

[75] Inventors: Alexander Klausener, Krefeld; Gerd Kleefeld, Duesseldorf; Dieter Berg, Wuppertal; Stefan Dutzmann, Duesseldorf; Gerd Hänbler, Leverkusen, all of Fed. Rep. of Germany

[73] Assignee: Bayer Aktiengesellschaft, Leverkusen, Fed. Rep. of Germany

[21] Appl. No.: 477,271

[22] Filed: Feb. 8, 1990

[30] Foreign Application Priority Data

Feb. 17, 1989 [DE] Fed. Rep. of Germany ....... 3904931

[51] Int. Cl.$^5$ .................. C07D 213/74; C07D 401/04; A01N 43/56; A01N 43/74
[52] U.S. Cl. .................................... 514/334; 514/336; 514/340; 514/341; 514/342; 514/347; 514/351; 514/357; 546/257; 546/275; 546/276; 546/277; 546/278; 546/279; 546/280; 546/284; 546/300; 546/301; 546/302; 546/312
[58] Field of Search .............. 546/300, 301, 302, 312, 546/257, 275, 276, 277, 278, 279, 280, 284

[56] References Cited

FOREIGN PATENT DOCUMENTS 0178826 4/1986 European Pat. Off. ............ 546/300
2270551 11/1987 Japan .................................. 546/312
2189485 10/1987 United Kingdom ................. 546/301

Primary Examiner—Frederick E. Waddell
Assistant Examiner—Zinna Northington Davis
Attorney, Agent, or Firm—Sprung, Horn, Kramer & Woods

[57] ABSTRACT

Fungicidal pyridyl-substituted acrylic esters of the formula

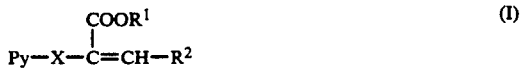 (I)

in which
$R^1$ represents alkyl or represents optionally substituted aralkyl,
$R^2$ represents dialkylamino or represents a radical $-Z-R^3$,
X represents oxygen or sulphur or represents a radical

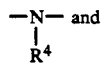 and Py represents optionally substituted pyridyl, where
$R^3$ represents alkyl or represents optionally substituted aralkyl,
$R^4$ represents hydrogen, alkyl or alkanoyl or represents in each case optionally substituted aralkyl or aryl and
Z represents oxygen or sulphur, their geometric isomers and isomer mixtures.

13 Claims, No Drawings

PESTICIDAL PYRIDYL-SUBSTITUTED ACRYLIC ESTER COMPOUNDS

The invention relates to new pyridyl-substituted acrylic esters, to several processes for their preparation, to their use in pesticides, and to intermediates, some of which are new.

It is known that certain substituted acrylic esters, such as, for example, the compound methyl 3-methoxy-2-(2-methylphenyl)-acrylate, have fungicidal properties (cf., for example, EP 178,826).

However, the activity of these previously known compounds is not entirely satisfactory in all fields of application, in particular when low application rates and concentrations are used.

New pyridyl-substituted acrylic esters of the general formula (I)

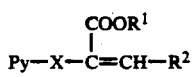
(I)

in which
- $R^1$ represents alkyl or represents optionally substituted aralkyl,
- $R^2$ represents dialkylamino or represents a radical $-Z-R^3$,
- X represents oxygen or sulphur or represents a radical

- Py represents optionally substituted pyridyl, where
- $R^3$ represents alkyl or represents optionally substituted aralkyl,
- $R^4$ represents hydrogen, alkyl or alkanoyl or represents in each case optionally substituted aralkyl or aryl and
- Z represents oxygen or sulphur, have been found.

The compounds of the formula (I) can be present as geometric isomers or isomer mixtures of various compositions. The invention covers both the pure isomers and the isomer mixtures.

Furthermore, it has been found that the new pyridyl-substituted acrylic esters of the general formula (I)

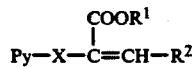
(I)

in which
- $R^1$ represents alkyl or represents optionally substituted aralkyl,
- $R^2$ represents dialkylamino or represents a radical $-Z-R^3$,
- X represents oxygen or sulphur or represents a radical

- Py represents optionally substituted pyridyl where
- $R^3$ represents alkyl or represents optionally substituted aralkyl,
- $R^4$ represents hydrogen, alkyl or alkanoyl, or represents in each case optionally substituted aralkyl or aryl and
- Z represents oxygen or sulphur, and their isomers or isomer mixtures, are obtained following one of the processes described below:

(a) pyridyl-substituted acrylic esters of the formula (Ia)

(Ia)

in which
$R^1$, $R^3$, X and Py have the abovementioned meanings, are obtained when hydroxyacrylic esters or their alkali metal salts of the formula (II)

(II)

in which
M represents hydrogen or represents an alkali metal cation and
$R^1$, X and Py have the abovementioned meanings, are reacted with alkylating agents of the formula (III)

(III)

in which
$E^1$ represents an electron-withdrawing leaving group and
$R^3$ has the abovementioned meaning,
if appropriate in the presence of a diluent and if appropriate in the presence of a reaction auxiliary;

(b) pyridyl-substituted acrylic esters of the formula (Ib)

(Ib)

in which
$R^{2-1}$ represents dialkylamino and
$R^1$, X and Py have the abovementioned meanings, are obtained when substituted acetic esters of the formula (IV)

(IV)

in which
$R^1$, X and Py have the abovementioned meanings, are reacted with formamides of the formula (Va)

(Va)

in which
$R^{2-1}$ has the abovementioned meaning, or with derivatives of these formamides of the formula (Vb)

(Vb)

in which $R^5$ and $R^6$ independently of one another each represent alkoxy or dialkylamino and $R^{2-1}$ has the abovementioned meaning, if appropriate in the presence of a diluent;

(c) pyridyl-substituted acrylic esters of the formula (Ic)

in which $X^1$ represents sulphur or represents a radical

and $R^1$, $R^3$ and Py have the abovementioned meanings, are obtained when oxailic acid derivatives of the formula (VI)

in which $R^1$, $X^1$ and Py have the abovementioned meanings, are reacted with organometal compounds of the formula (VII)

in which $R^3$ has the abovementioned meaning, if appropriate in the presence of a diluent;

(d) pyridyl-substituted acrylic esters of the formula (Id)

in which $R^1$, $R^3$ and Py have the abovementioned meanings, are obtained when substituted acrylic esters of the formula (VIII)

in which $E^2$ represents an electron-withdrawing leaving group and $R^1$ and Py have the abovementioned meanings, are reacted with thiols of the formula (IX)

      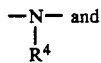

in which $R^3$ has the abovementioned meaning, if appropriate in the presence of a diluent and if appropriate in the presence of a reaction auxiliary.

Finally, it has been found that the new pyridylsubstituted acrylic esters of the general formula (I) have good action against pests.

Surprisingly, the substituted acrylic esters of the general formula (I) according to the invention show a considerably better fungicidal activity, for example, than the acrylic esters known from the prior art, such as, for example, the compound methyl 3-methoxy-2-(2-methylphenyl)-acrylate, which are compounds of similar chemical structure and have a similar type of action.

Formula (I) provides a general definition of the pyridyl-substituted acrylic esters according to the invention. Preferred compounds of the formula (I) are those in which $R^1$ represents straight-chain or branched alkyl which has 1 to 6 carbon atoms, or represents aralkyl which has 1 to 4 carbon atoms in the straight-chain or branched alkyl moiety and 6 to 10 carbon atoms in the aryl moiety and which is optionally monosubstituted to polysubstituted in the aryl moiety by identical or different substituents, suitable aryl substituents being: halogen, cyano, nitro, in each case straight-chain or branched alkyl, alkoxy or alkylthio, each having 1 to 4 carbon atoms, in each case straight-chain or branched halogenoalkyl, halogenoalkoxy or halogenoalkylthio, each having 1 to 4 carbon atoms and 1 to 9 identical or different halogen atoms, in each case straight-chain or branched alkoxycarbonyl or alkoximinoalkyl, each having 1 to 8 carbon atoms in the individual alkyl moieties, cycloalkyl which has 3 to 7 carbon atoms, double-linked alkanediyl which has 3 to 5 carbon atoms, aryl, aralkyl, aryloxy or aralkyloxy, each of which has 6 to 10 carbon atoms in the aryl moiety and if appropriate 1 to 4 carbon atoms in the straight-chain or branched alkyl moiety and each of which is optionally monosubstituted to polysubstituted in the aryl moiety by identical or different substituents from the series comprising halogen, alkyl, alkoxy, alkylthio, halogenoalkyl, halogeno-alkoxy or halogenoalkylthio, each having 1 to 4 carbon atoms and if appropriate 1 to 9 identical or different halogen atoms, or heteroarylalkyl or heteroaryl, each of which has 2 to 9 carbon atoms and 1 to 4 identical or different hetero atoms—in particular nitrogen, oxygen and/or sulphur—in the heteroaryl moiety and if appropriate 1 to 4 carbon atoms in the straight-chain or branched alkyl moiety and each of which is optionally monosubstituted to polysubstituted in the heteroaryl moiety by identical or different substituents from the series comprising halogen, alkyl, alkoxy, alkylthio, halogenoalkyl, halogenoalkoxy or halogenoalkylthio, each having 1 to 4 carbon atoms and if appropriate 1 to 9 identical or different halogen atoms;

$R^2$ represents dialkylamino which has 1 to 6 carbon atoms in each of the individual alkyl moieties, or represents a radical $—Z—R^3$, X represents oxygen or sulphur or represents a radical —N— and
|
$R^4$ Py represents 2-pyridyl, 3-pyridyl or 4-pyridyl, each of which is monosubstituted to polysubstituted by identical or different substituents, suitable substituents in each case being: halogen, cyano, nitro, in each case straight-chain or branched alkyl, alkoxy or alkylthio, each having 1 to 6 carbon atoms, in each case straight-chain or branched halogenoalkyl, halogenoalkoxy or halogenoalkylthio, each having 1 to 4 carbon atoms and 1 to 9 identical or different halogen atoms, in each case straight-chain or branched alkoxycarbonyl, alkoximinoalkyl, dialkylamino or dialkylaminocarbonyl, each having 1 to 4 carbon atoms in the individual alkyl moieties, in each case straight-chain or branched alkenyl or alkinyl, each having 2 to 8 carbon atoms, or aryl, aryloxy, arylthio, arylcarbonyl, aralkyl, aralkenyl, aralkinyl, aralkyloxy or heteroaryl, each of which has 6 to 10 carbon atoms in the aryl moiety and if appropriate 1 to 6 carbon atoms in the straight-chain or branched alkyl moiety or if appropriate 2 to 6 carbon atoms in the straight-chain or branched alkenyl moiety or alkinyl moiety or 2 to 9 carbon atoms and 1 to 4 identical or different hetero atoms—in particular nitrogen, oxygen and/or sulphur—in the heteroaryl moiety and each of which is optionally monosubstituted to polysubstituted in the respective aryl moiety or in the heteroaryl moiety by identical or different substituents from the series comprising halogen, alkyl, alkoxy, alkylthio, halogenoalkyl, halogenoalkoxy, halogenoalkylthio, dioxyalkylene, halogensubstituted dioxyalkylene or optionally substituted phenyl; where $R^3$ represents straight-chain or branched alkyl which has 1 to 6 carbon atoms or represents aralkyl which has 1 to 4 carbon atoms in the straight-chain or branched alkyl moiety and 6 to 10 carbon atoms in the aryl moiety and which is optionally monosubstituted to polysubstituted in the aryl moiety by identical or different substituents, suitable substituents being the aryl substituents mentioned in the case of $R^1$, represents hydrogen, or represents straight-chain or branched alkyl which has 1 to 6 carbon atoms, or represents straight-chain or branched alkanoyl which has 1 to 6 carbon atoms in the alkyl moiety, or represents aralkyl or aryl which has 1 to 6 carbon atoms in the straight-chain or branched alkyl moiety and 6 to 10 carbon atoms in the respective aryl moiety and each of which is optionally monosubstituted to polysubstituted in the respective aryl moiety by identical or different substituents, suitable substituents in the aryl moiety in each case being those mentioned in the case of $R^1$ and, Z represents oxygen or sulphur.

Particularly preferred compounds of the formula (I) are those in which $R^1$ represents methyl, ethyl, n- or i-propyl or n-, i-, s- or t-butyl, or represents benzyl which is optionally monosubstituted to trisubstituted by identical or different substituents, suitable substituents being: fluorine, chlorine, bromine, cyano, nitro, methyl, ethyl, n- or i-propyl, n-, i-, s- or tbutyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl or 1,4-butanediyl, or phenyl, benzyl, phenoxy or benzyloxy, each of which is optionally monosubstituted to trisubstituted in the phenyl moiety by identical or different substituents from the series comprising fluorine, chlorine, bromine, methyl, ethyl, methoxy, ethoxy, methylthio, trifluoromethyl, difluoromethoxy, trifluoromethoxy and/or trifluoromethylthio, $R^2$ represents dialkylamino which has 1 to 4 carbon atoms in each of the individual alkyl moieties, or represents a radical —Z—$R^3$, X represents oxygen or sulphur or represents a radical

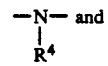

Py represents 2-pyridyl, 3-pyridyl or 4-pyridyl, each of which is optionally monosubstituted to trisubstituted by identical or different substituents, at least one substituent in each case representing phenyl, naphthyl, phenoxy, phenylthio, phenylcarbonyl, benzyl, phenylethyl, phenylpropyl, phenylethenyl, benzyloxy or heteroaryl, each of which is optionally monosubstituted to trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, ethylthio, trifluoromethyl,-trifluoromethoxy,trifluoromethylthio, dioxymethylene, or by phenyl which is optionally monosubstituted to trisubstituted by identical or different substituents from the series comprising fluorine, chlorine, methyl, methoxy or trifluoromethyl, suitable specific heteroaryl radicals being the following:

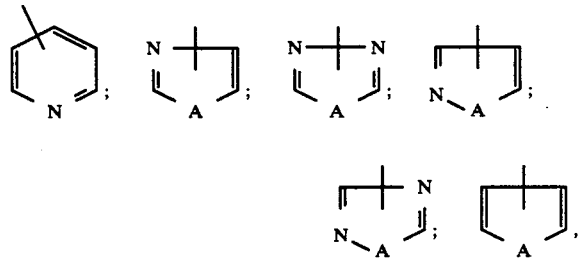

which can also be benzo-fused, if appropriate, and in which

A in each case represents oxygen or sulphur or represents an NH group; moreover, the following are preferably suitable as further pyridyl substituents: fluorine, chlorine, bromine, cyano, nitro, methyl, ethyl, n- or i-propyl, n-, i-, s- or t-butyl, methoxy, ethoxy, n-or i-propoxy, methylthio, trifluoromethyl, trifluoromethoxy, trifluoromethylthio, methoxycarbonyl, methoximinoethyl, ethoximinoethyl, dimethylamino, diethylamino, dimethylcarbamoyl, diethylcarbamoyl, allyl, butenyl or propargyl; and where $R^3$ represents methyl, ethyl, n- or i-propyl, or n-, i-, s- or t-butyl, or represents benzyl which is optionally monosubstituted to trisubstituted by identical or different substituents, suitable substituents being those mentioned in the case of $R^1$ and $R^2$;

$R^4$ represents hydrogen, methyl, ethyl, n- or i-propyl or n-, i-, s- or t-butyl, or represents acetyl, propionyl or n- or i-butyryl or represents benzyl or phenyl, each of which is optionally monosubstituted to trisubstituted by identical or different substituents, suitable substituents being those mentioned in the case of $R^1$ and $R^2$, and Z represents oxygen or sulphur.

Very particularly preferred compounds of the formula (I) are those in which $R^1$ represents methyl or ethyl, $R^2$ represents methoxy or ethoxy, X represents oxygen or sulphur or represents a radical

Py represents 2-pyridyl, 3-pyridyl or 4-pyridyl, each of which is optionally monosubstituted to trisubstituted by identical or different substituents, at least one substituent in each case representing benzo-fused phenyl, phenoxy, phenylcarbonyl, benzyl, pyridyl, pyrazolyl, oxazolyl, thiazolyl, thienyl, furyl, thiadiazolyl, oxadiazolyl, imidazolyl or triazolyl, each of which is optionally monosubstituted to trisubstituted by identical or different substituents from the series comprising fluorine, chlorine, methyl, ethyl, methoxy, trifluoromethyl, dioxymethylene or phenyl, suitable further pyridyl substituents in each case being: fluorine, chlorine, bromine, cyano, nitro, methyl, ethyl, methoxy, methylthio, trifluoromethyl, trifluoromethoxy, trifluoromethylthio, methoxycarbonyl, ethoxycarbonyl or dimethylamino, and $R^4$ represents methyl, ethyl or benzyl.

Aryl as such or in compositions denotes phenyl or naphthyl, in particular phenyl.

All aliphatic radicals as such or in compositions are straight-chain or branched.

Halogen represents fluorine, chlorine, bromine or iodine, in particular represents fluorine, chlorine or bromine, unless defined otherwise.

The following pyridyl-substituted acrylic esters of the general formula (I) may be mentioned individually, in addition to the compounds mentioned in the Preparation Examples:

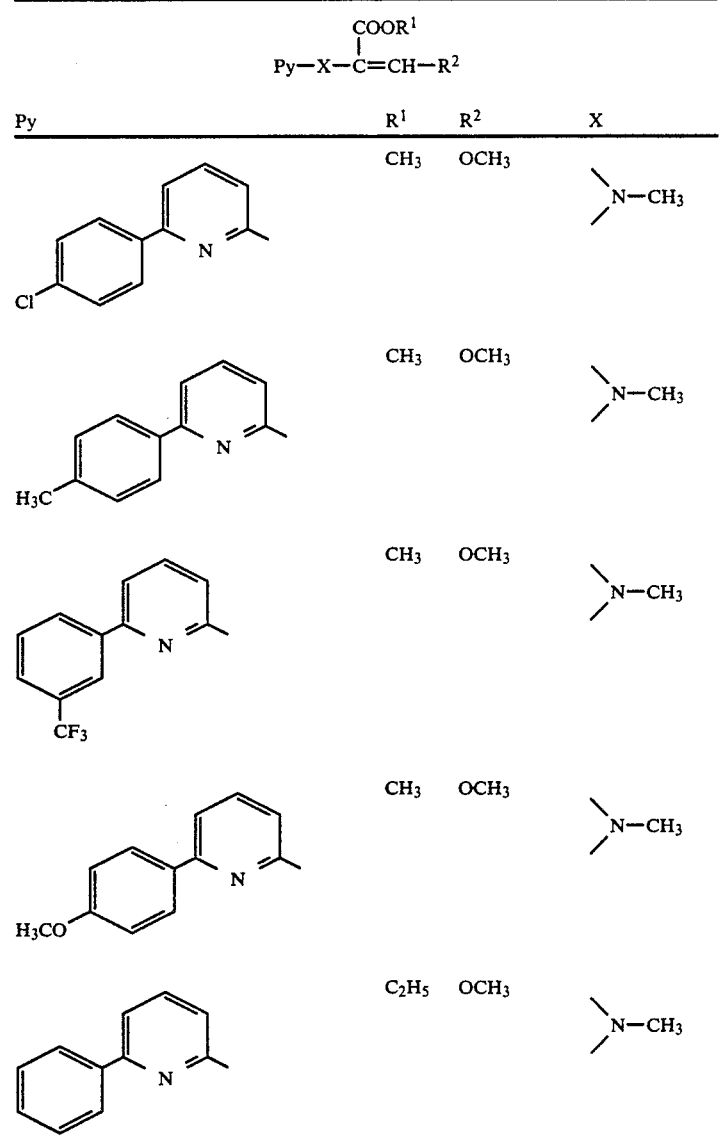

-continued
$$Py-X-\underset{\underset{COOR^1}{|}}{C}=CH-R^2$$
| Py | R¹ | R² | X |
|---|---|---|---|
| 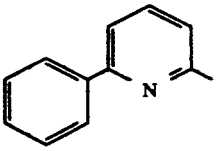 | C₂H₅ | OC₂H₅ |  |
| 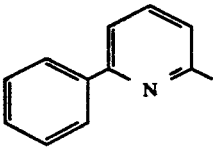 | CH₃ | OCH₃ |  |
| 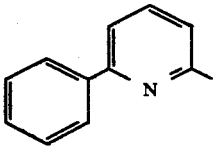 | CH₃ | —N(CH₃)₂ |  |
| 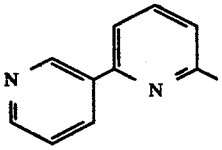 | CH₃ | OC₂H₅ |  |
| 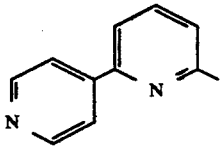 | CH₃ | OCH₃ |  |
| 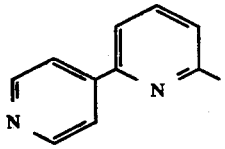 | CH₃ | OC₂H₅ |  |
| 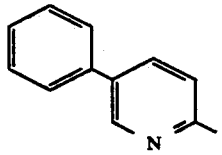 | CH₃ | OCH₃ |  |
| 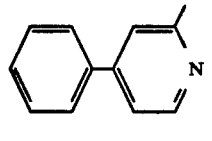 | CH₃ | OCH₃ |  |
| 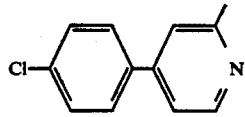 | CH₃ | OCH₃ |  |

-continued
$$Py-X-\underset{\underset{\displaystyle COOR^1}{|}}{C}=CH-R^2$$
| Py | R¹ | R² | X |
|---|---|---|---|
| 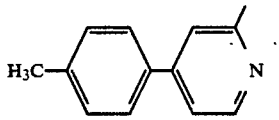 | CH₃ | OCH₃ |  |
| 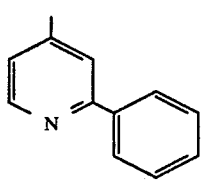 | CH₃ | OCH₃ |  |
| 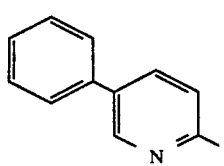 | CH₃ | OCH₃ | S |
| 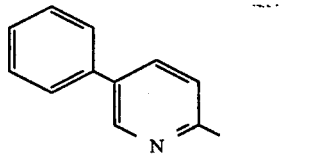 | CH₃ | OCH₃ |  |
| 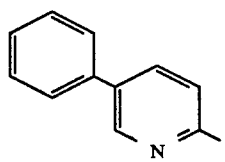 | CH₃ | OCH₃ | 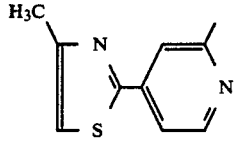 |
|  | CH₃ | OCH₃ | O |
| 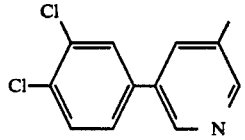 | CH₃ | OCH₃ | 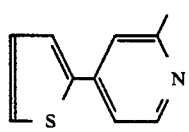 |
| (Cl, Cl-phenyl-pyridine) | CH₃ | OCH₃ | S |
| (thienyl-pyridine) | CH₃ | OCH₃ | O |

-continued $$Py-X-\underset{\underset{CH-R^2}{\parallel}}{\overset{\overset{COOR^1}{|}}{C}}$$

| Py | R¹ | R² | X |
|---|---|---|---|
| 2-phenylpyridin-4-yl | CH₃ | OCH₃ | S |
| 2-(4-chlorophenyl)pyridin-4-yl | CH₃ | OCH₃ | N-CH₃ |
| 2-(thien-2-yl)pyridin-4-yl | CH₃ | OCH₃ | N-CH₃ |
| 6-methyl-2-(1-methyl-2-thioxoethylidene)pyridinyl | CH₃ | OCH₃ | N-CH₃ |
| 6-methyl-2-[(4-methoxyphenyl)thiomethylene]pyridinyl | CH₃ | OCH₃ | N-CH₃ |
| 2-chloro-6-methyl-4-(t-butylthiomethylene)pyridinyl | CH₃ | OCH₃ | S |
| 2-[(4-chlorophenyl)ethynyl]-6-methylpyridinyl | CH₃ | OCH₃ | N-CH₃ |
| 6-methyl-2-phenylpyridin-3-yl (biphenyl-pyridine) | CH₃ | OCH₃ | O |
| 3-methyl-4-methyl-2-phenylpyridinyl | CH₃ | OCH₃ | S |

-continued $$Py-X-\underset{\underset{COOR^1}{|}}{C}=CH-R^2$$

| Py | R¹ | R² | X |
|---|---|---|---|
| 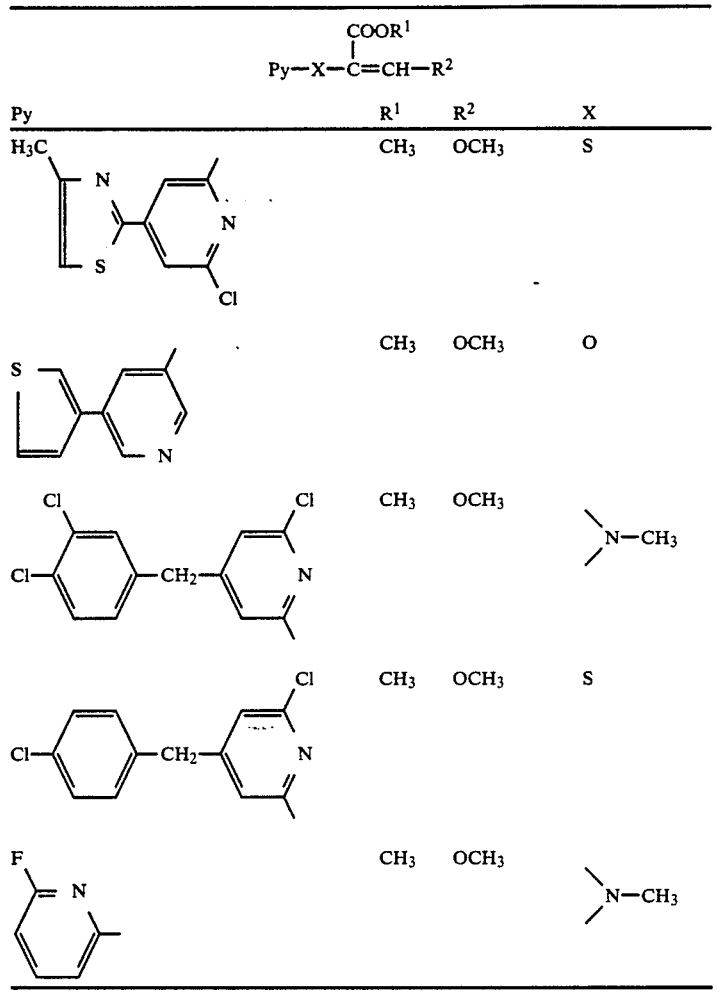 | CH₃ | OCH₃ | S |
| | CH₃ | OCH₃ | O |
| | CH₃ | OCH₃ | $\diagdown$N—CH₃ $\diagup$ |
| | CH₃ | OCH₃ | S |
| | CH₃ | OCH₃ | $\diagdown$N—CH₃ $\diagup$ |

If, for example, methyl 2-{N-[6-(4-chlorophenyl)-pyridin-2-yl]-N-methylamino}-3-hydroxy-acrylate and dimethyl sulphate are used as starting substances, the course of the reaction of process (a) according to the invention may be represented by the following equation:

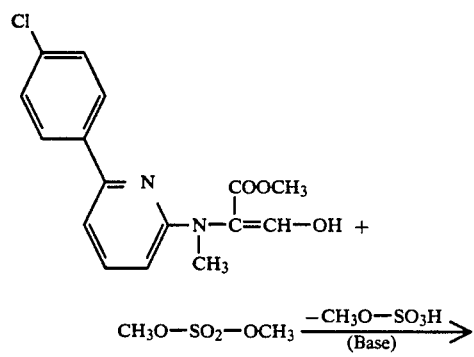

$$CH_3O-SO_2-OCH_3 \xrightarrow[\text{(Base)}]{-CH_3O-SO_3H}$$

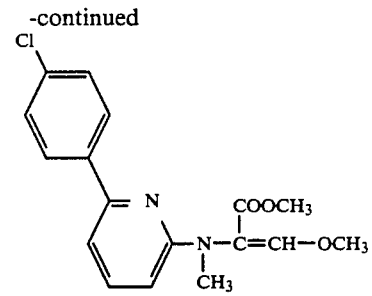

If, for example, methyl 2-{5-(4-methylphenyl)-pyridin-2-yloxy}-acetate and dimethylformamide dimethylacetal are used as starting substances, the course of the reaction of process (b) according to the invention may be represented by the following equation:

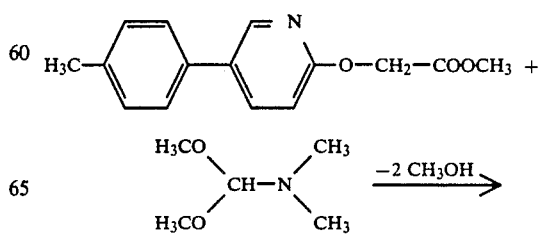

$$\xrightarrow{-2\ CH_3OH}$$

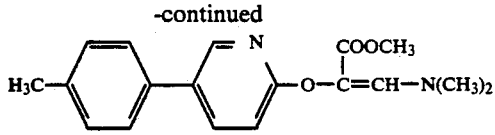

If, for example, 2-[2-(4-fluorophenyl)-pyrdin-4ylthio]-2-oxo-acetate and (methylthio)-(trimethylsilyl)-methylenelithium are used as starting substances, the course of the reaction of process (c) according to the invention may be represented by the following equation:

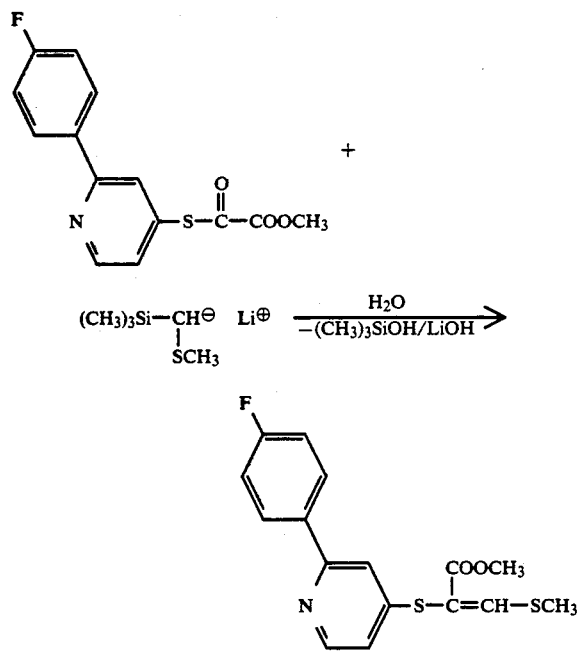

If, for example, methyl 3-methylsulphonyloxy-2-(5-phenylppyridin-2yloxy)-acrylate and methylmercaptan are used as starting substances, the course of the reaction of process (d) according to the invention may be represented by the following equation:

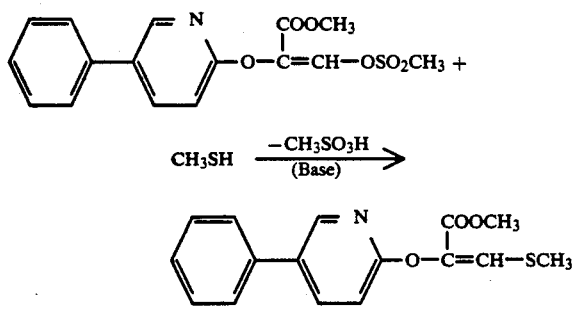

Formula (II) provides a general definition of the hydroxyacrylic esters or their alkali metal salts required as starting substances for carrying out process (a) according to the invention. In this formula (II), $R^1$ and Py preferably represent those radicals which have already been mentioned in connection with the description of the substances of the formula (I) according to the invention as being preferred for these substituents.

M preferably represents hydrogen or represents a sodium or potassium cation.

Some of the hydroxyacrylic esters of the formula (II) are known (cf. EP 83,186 or U.S. Pat. No. 4,468,399).

Compounds of the formula (IIa)

in which
$R^1$, Py, X and M have the abovementioned meanings, were hitherto unknown and also form the subject of the invention, with the exception of the compound ethyl 2-(6-methylpyrid-3-yloxy)-3-hydroxyacrylate.

They are obtained when substituted acetic esters of the formula (IV)

$$Py-X-CH_2-COOR \qquad (IV)$$

in which
$R^1$, Py and X have the abovementioned meanings, with the exception of the compound ethyl 2-(6-methylpyrid-3-yloxy)-acetate,
are reacted with formic esters of the formula (X)

in which
$R^7$ represents alkyl, in particular represents methyl or ethyl, if appropriate in the presence of a diluent, such as, for example, dimethylformamide, and if appropriate in the presence of a basic reaction auxiliary, such as, for example, sodium hydride, at temperatures between $-20°$ C. and $+50°$ C.

Formic esters of the formula (X) are generally known compounds of organic chemistry.

Formula (III) provides a general definition of the alkylating agents furthermore required as starting substances for carrying out process (a) according to the invention. In this formula (III), $R^3$ preferably represents those radicals which have already been mentioned in connection with the description of the substances of the formula (I) according to the invention as being preferred for this substituent.

$E^1$ represents a leaving group customary in the case of alkylating agents, preferably represents an optionally substituted alkyl radical, alkoxy radical or arylsulphonyloxy radical, such as, for example, a methoxysulphonyloxy radical, an ethoxysulphonyloxy radical or a p-toluenesulphonyloxy radical, or represents halogen, in particular represents chlorine, bromine or iodine.

The alkylating agents of the formula (III) are generally known compounds of organic chemistry.

Formula (IV) provides a general definition of the substituted acetic esters required as starting substances for carrying out process (b) according to the invention and for the synthesis of the precursors of formula (II). In this formula (IV), $R^1$, X and Py preferably represent those radicals which have already been mentioned in connection with the description of the substances of the formula (I) according to the invention as preferred for these substituents.

Some of the substituted acetic esters of the formula (IV) are known or can be obtained in analogy to known processes (cf., for example, J Chem. Pharm. Bull. 23, 3008–3010 [1975]; Prakt. Chem. 315, 1175–1182 [1973]; Chimia 28, 235–236 [1974]; Fak. J. Sci. Ind. Res. 20, 139–149 [1977]; J. Heterooycl. Chem. 5, 281–283 [1968]; Fol. J. Chem. 53, 2349–2354 [1979]; J. Heterocycl. Chem. 24, 85–89 [1987]; Zh. org. Khim. 20, 1317–1538 [1984]; Zh. Org. Khim. 20, 2002–2011 [1984]; Izv. Akad. Nauk SSSR. Ser. Khim. 1984, 2760–2765; DE 2,103,728; DE 2,637,911; DE 2,709,108; DE 2,725,361; DE 2,425,282; GB 1,161,492 [1969; EP 182,769,; EP 245,230; EP 227,932).

Compounds which are not yet known and are also part of the invention are those of the formula (IVa)

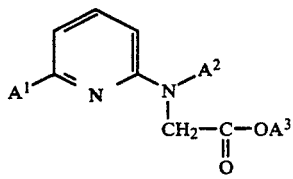

(IVa)

in which
- $A^1$ represents phenyl, naphthyl, pyridyl, pyrimidinyl, pyrazinyl, pyridazinyl, thienyl, furanyl, pyrrolyl, thiazolyl, pyrazolyl or oxazolyl, each of which is unsubstituted or mono-or polysubstituted by identical or different substituents, substituents which may be mentioned in each case being; halogen, methyl, ethyl, n- or i-propyl, n-, i-, s- or t-butyl, methoxy, ethoxy, n- or i-propoxy, n-, i-, s- or t-butoxy, halogenalkyl having 1 or 2 carbon atoms and 1 to 5 identical or different fluorine or chlorine atoms, methylthio, ethylthio, n- or i-propylthio, n-, i-, s- or t-butylthio, alkylidendioxy having 1 to 3 carbon atoms, or phenyl which is unsubstituted or mono- or polysubstituted by identical or different substituents from the group comprising methyl, ethyl, methoxy, ethoxy, halogen, and halogenomethyl having 1 to 3 identical or different fluorine or chlorine atoms,
- $A^1$ furthermore represents phenoxy which is unsubstituted or mono- or polysubstituted by identical or different substituents, possible substituents being halogen, phenoxy, methyl, ethyl or n- or i-propyl, or represents a grouping —C≡C—$A^4$ or —CH=CH—$A^4$,
- $A^2$ represents methyl, ethyl, n- or i-propyl, or n-, i-, s- or t-butyl,
- $A^3$ represents methyl, ethyl, n- or i-propyl, or n-, i-, s- or t-butyl and
- $A^4$ represents unsubstituted or substituted phenyl, possible substituents being the substituents mentioned above under $A^1$.

It has furthermore been found that the new compounds of the formula (IVa) have powerful fungicidal activity.

Particularly preferred compounds of the formula (IVa) are those in which
- $A^1$ represents phenyl, naphthyl, pyridyl, thienyl or thiazolyl, which are in each case unsubstituted or mono-, di- or tri-substituted by identical or different substituents, substituents which may be mentioned in each case being: fluorine, chlorine, bromine, methyl, ethyl, methoxy, ethoxy, trifluoromethyl, difluoromethyl, dichlorofluoromethyl, chlorodifluoromethyl, methylthio, methylenedioxy or phenyl which is unsubstituted or mono-, di- or tri-substituted by identical or different substituents from the group comprising methyl, fluorins, chlorine, methoxy and trifluoromethyl,
- $A^1$ also represents phenoxy which is unsubstituted or mono-, di- or tri-substituted by identical or different substituents, possible substituents being fluorine, chlorine, bromine, phenoxy, methyl or ethyl, or represents a grouping —C≡C—$A^4$ or —CH=CH—$A^4$,
- $A^2$ represents methyl or ethyl,
- $A^3$ represents methyl, ethyl, n- or i-propyl and
- $A^4$ represents unsubstituted or substituted phenyl, possible substituents being those mentioned above under $A^1$.

The new compounds of the formula (IVa)

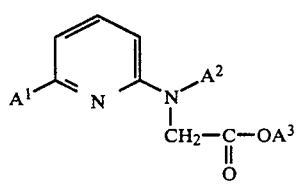

(IVa)

in which
$A^1$, $A^2$ and $A^3$ have the abovementioned meaning, are obtained (α) by reacting substituted halogenopyridines of the formula (XIV)

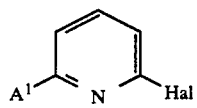

(XIV)

in which
$A^1$ has the abovementioned meaning and Hal represents chlorine or bromine,
with amino acid derivatives of the formula (XV)

$$A^2-NH-CH_2-COOA^3 \quad (XV)$$

in which
$A^2$ and $A^3$ have the abovementioned meaning,
if appropriate in the presence of a diluent and if appropriate in the presence of a base, (β) by reacting substituted aminopyridines of the formula (XVI)

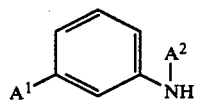

(XVI)

in which
$A^1$ and $A^2$ have the abovementioned meaning,
with halogenocarboxylic acid esters of the formula (XVII)

$$Hal-CH_2-COOA^3 \quad (XVII)$$

in which
$A^3$ has the abovementioned meaning and Hal represents chlorine or bromine,
if appropriate in the presence of a diluent and if appropriate in the presence of a base.

The halogenopyridines of the formula (XIV), the amino acid derivatives of the formula (XV), the aminopyridines of the formula (XVI) and the halogenocarboxylic acid esters of the formula (XVII) are generally known compounds of organic chemistry.

The preparation of the compounds of the formula (IVa) according to the invention by process variants (α) and (β) is preferably carried out using diluents. Possible diluents are virtually all inert organic solvents. These preferably include ethers such as diethyl and dibutyl ether glycol dimethyl ether and diglycol dimethyl ether, tetrahydrofuran and dioxane and amides, such as, for example, dimethylformamide, dimethylacetamide and N-methylpyrrolidone.

Suitable bases are alkali met(al carbonates, such as sodium and potassium carbonate, or tertiary amines, such as, for example, triethylamine, N,N-dimethylaniline and pyridine.

The reaction temperatures can be varied within a wide range for the preparation of the compounds of the formula (IVa) according to the invention by process variants (α) and (β). In general,(these variants are carried out at temperatures between 50° C. and +200° C., preferably between 75° C. and +150° C. and particularly preferably at the reflux temperature of the respective solvent.

For carrying out the process according to process variants (α) and (β) the starting compounds are generally employed in equimolar quantities. It is however also possible to use one of the two components employed in a relatively large excess. The reaction mixture is stirred for several hours at the temperature required in each case. The working up and isolation of the products is carried out by customary methods.

Formulae (Va) and (Vb) provide general definitions of the formamides and their derivatives furthermore required as starting substances for carrying out process (b) according to the invention. In these formulae (Va) and (Vb), $R^{2-1}$ preferably represents dialkylamino having 1 to 6, in particular 1 to 4, carbon atoms in each of the individual straight-chain or branched alkyl moieties. $R^{2-1}$ very particularly preferably represents. dimethylamino or diethylamino.

$R^5$ and $R^6$ independently of one another preferably represent in each case straight-chain or branched alkoxy having 1 to 4 carbon atoms, in particular represent methoxy or ethoxy, or represent a dialkylamino radical having 1 to 6, in particular 1 to 4, carbon atoms in each of the individual straight-chain or branched alkyl moieties.

The formamides of the formula (Va) and their derivatives of the formula (Vb) are generally known compounds of organic chemistry.

Formula (VI) provides a general definition of the oxalic acid derivatives required as starting substances for carrying out process (c) according to the invention. In this formula (VI), $R^1$ and Py preferably represent those radicals which have already been mentioned in connection with the description of the substances of the formula (I) according to the invention as being preferred for these substituents.

$X^1$ preferably represents sulphur or represents a radical

where $R^4$ preferably represents those radicals which have already been mentioned in connection with the description of the substances of the formula (I) according to the invention as being preferred for this substituent.

The oxalic acid derivatives of the formula (VI) are known in most cases or can be obtained in analogy to known processes (cf., for example, J. chem. Soc. C, 1969, 1505-1514; J. med. Chem. 27, 125-128 [1984]; U.S. Pat. No. 4,036,839; U.S. Pat. No. 4,160,100; Synthetic Communications 11, 943 [1981] or Organic Reactions, 26, 1 [1979]), for example when oxalic esters of the formula (XI)

in which
$E^3$ represents alkoxy or halogen, in particular represents methoxy, ethoxy or chlorine and
$R^1$ has the abovementioned meaning are reacted with heterocyclic compounds of the formula (XII)

in which
Py and $X^1$ have the abovementioned meaning, if appropriate in the presence of a diluent, such as, for example, dichloromethane or tetrahydrofuran, and if appropriate in the presence of a base, such as, for example, n-butyllithium, sodium hydride, potassium t-butoxide, triethylamine or pyridine, at temperatures between −80° C. and +80° C.

Oxalic esters of the formula (XI) are generally known compounds of organic chemistry.

Heterocyclic compounds of the formula (XII) are likewise generally known or can be obtained in analogy to generally known processes.

Formula (VII) provides a general definition of the organometal compounds furthermore required as starting substances for carrying out process (c) according to the invention. In this formula (VII), $R^3$ preferably represents those radicals which have already been mentioned in connection with the description of the substances of the formula (I) according to the invention as being preferred for these substituents.

The organometal compounds of the formula (VII) are known (cf., for example, J. org. Chem. 33, 780 [1968]; J. org. chem. 37, 939 [1972]).

Formula (VIII) provides a general definition of the substituted acrylic esters required as starting substances for carrying out process (d) according to the invention. In this formula (VIII), $R^1$ and Py preferably represent those radicals which have already been mentioned in connection with the description of the substances of the formula (I) according to the invention as being preferred for these substituents.

$E^2$ preferably represents a suitable acyloxy radical or sulphonyloxy radical, in particular represents an acetoxy radical, a methanesulphonyloxy radical or a p-toluenesulphonyloxy radical.

The substituted acrylic esters of the formula (VIII) were hitherto unknown.

They are obtained when hydroxyacrylic esters of the formula (IIb)

in which

R¹ and Py have the abovementioned meaning are reacted with acid chlorides of the formula (XIII)

$$R^8—Cl \quad \text{(XIII)}$$

in which

R⁸ represents an acyl radical or a sulphonyl radical, in particular represents an acetyl radical, a methanesulphonyl radical or a p-toluenesulphonyl radical, if appropriate in the presence of a diluent, such as, for example, dichloromethane, and if appropriate in the presence of an acid-binding agent, such as, for example, triethylamine or pyridine, at temperatures between −20° C. and +120° C.

Acid chlorides of the formula (XIII) are generally known compounds of organic chemistry.

Formula (IX) provides a general definition of the thiols furthermore required as starting substances for carrying out process (d) according to the invention. In this formula (IX), R³ preferably represents those radicals which have already been mentioned in connection with the description of the substances of the formula (I) according to the invention as being preferred for these substituents.

The thiols of the formula (IX) are generally known compounds of organic chemistry.

Suitable diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or sulphoxides, such as dimethyl sulphoxide.

If appropriate, process (a) according to the invention can also be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-C₁₃/C₁₅-alkylammonium chloride, dibenzyl-di-methyl-ammonium methylsulphate, dimethyl-C₁₂/C₁₄-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (a) according to the invention is preferably carried out in the presence of a suitable basic reaction auxiliary. Suitable reaction auxiliaries are all inorganic and organic bases which can customarily be used. The hydrides, hydroxides, amides, alkoxides, carbonates or hydrogen carbonates of alkali metals, such as, for example, sodium hydride, sodium amide, sodium hydroxide, sodium methoxide, sodium ethoxide, potassium t-butoxide, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

When carrying out process (a) according to the invention, the reaction temperatures can be varied within a substantial range. In general, the process is carried out at temperatures between −30° C. and +120° C., preferably at temperatures between −20° C. and +60° C.

For carrying out process (a) according to the invention, 1.0 to 10.0 moles, preferably 1.0 to 5.0 moles, of alkylating agent of the formula (III) and if appropriate 1.0 to 5.0 moles, preferably 1.0 to 2.0 moles, of reaction auxiliary are generally employed per mole of 3-hydroxyacrylic ester or of a corresponding alkali metal salt of the formula (II).

In this connection, it is also possible to prepare the hydroxyacrylic esters or their alkali metal salts of the formula (II) required a starting compounds for carrying out process (a) according to the invention in a previous reaction directly in the reaction vessel, and to subsequently react the products further without isolation according to process (a) according to the invention (one-pot variant). The reaction is carried out and the reaction products are worked up and isolated by generally customary methods (cf. also the Preparation Examples).

Suitable diluents for carrying out process (b) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, or ethers, such as diethyl ether, dioxane, tetrahydrofuran or ethylene glycol dimethyl ether or ethylene glycol diethyl ether.

However, it is also possible to carry out process (b) according to the invention without adding a diluent.

When carrying out process (b) according to the invention, the reaction temperatures can be varied within a substantial range. In general, the process is carried out at temperatures between −20° C. and +200° C., preferably at temperatures between 0° C. and 150° C.

For carrying out process (b) according to the invention, 1.0 to 30.0 moles, preferably 1.0 to 15.0 moles, of formamide, of the formula (Va) or of a corresponding derivative of the formula (Vb) are generally employed per mole of substituted acetic ester of the formula (IV). The reaction is carried out and the reaction products are worked up and isolated by generally customary methods (cf. in this context also G. Mathieu; J. Weill-Raynal "Formation of C-C-Bonds-, vol. I; p. 229–244; Thieme Verlag Stuttgart 1973).

Suitable diluents for carrying out process (c) according to the invention are inert organic solvents. These include, in particular, aliphatic, alicyclic or aromatic hydrocarbons, such as, for example, benzine, benzene, toluene, xylene, petroleum ether, hexane or cyclohexane, or ethers, such as diethyl ether, dioxane, tetrahydrofuran or ethylene glycol dimethyl ether or ethylene glycol diethyl ether.

When carrying out process (c) according to the invention, the reaction temperatures can be varied within a substantial range. In general, the process is carried out at temperatures between −100° C. and +100° C., preferably at temperatures between −80° C. and +50° C.

For carrying out process (c) according to the invention, 1.0 to 1.5 moles, preferably 1.0 to 1.2 moles, of organometal compound of the formula (VII) are generally employed per mole of oxalic acid derivative of the formula (VI). The reaction is carried out and the reaction products are worked up and isolated by known methods (cf., for example, J. org. Chem. 33, 780 [1968]; J. org. Chem. 37; 939 [1972]).

Suitable diluents for carrying out process (d) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (d) according to the invention is preferably carried out in the presence of a suitable reaction auxiliary. Suitable auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, or tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (d) according to the invention, the reaction temperatures can be varied within a substantial range. In general, the process is carried out at temperatures between −20° C. and 180° C., preferably at temperatures between 0° C. and 150° C.

Depending on the boiling point of the reactant used, for example when lower-boiling thiols of the formula (IX) are employed, the process according to the invention can also be carried out under pressure, if appropriate. In this case, it is preferred to carry out the process at the pressure which is established under the reaction conditions when the mixture is heated to the required reaction temperature.

For carrying out process (d) according to the invention, 1.0 to 20.0 moles, preferably 1.0 to 5.0 moles, of thiol of the formula (IX) and if appropriate 1.0 to 5.0 moles, preferably 1.0 to 1.5 moles, of reaction auxiliary are generally employed per mole of substituted acrylic ester of the formula (VIII). The reaction is carried out and the reaction products are worked up and isolated by generally customary methods.

The active substances according to the invention have a powerful action against pests and can be employed in practice for combating undesired harmful organisms. The active substances are suitable, for example for use as plant protection agents in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophhora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this connection, the active compounds according to the invention can be employed with particularly good success for combating cereal diseases, such as, for example, against the pathogen causing powdery mildew of cereals (Erysiphe graminis) or the pathogen causing leaf spot of wheat (Leptosphaeria nodorum) or the pathogen causing net blotch of barley (Pyrenophora teres) or for combating rice diseases, such as, for example, the pathogen causing rice blast disease (Pyricularia oryzae), or for combating diseases in fruit and vegetable growth, such as, for example, Oomycetes.

Depending on their particular physical and/or chemical properties, the active compounds can converted into the customary formulations, such as solutions, emulsions, suspensions, powders, foams, pastes, granules, aerosols, very fine capsules in polymeric substances and in coating compositions for seed, as well as ULV cold and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospho-lipids, can be used in the formulations. Other additives can be mineral and vegetable oils.

It is possible to use colorants such as inorganic pigments, for example iron oxide, titanium oxide and Prussian Blue, and organic dyestuffs, such as alizarin diestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

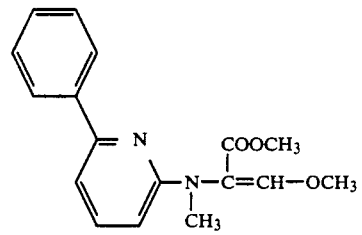

[Process (a) - one-pot variant]

A solution of 9.0 g (0.032 mol) of methyl N-methyl-N-(6-phenyl-2-pyridinyl)-aminoacetate in 50 ml of methyl formate is added dropwise at 5° C.–10° C. with stirring and under an argon protective gas atmosphere in the course of 1 hour to a suspension of 2.3 g (0.1 mol) of sodium hydride in 40 ml of dimethylformamide, the mixture is subsequently stirred for 20 hours at room temperature, 11 g (0.09 mol) of dimethyl sulphate are then added with cooling, and the mixture is stirred for a further 24 hours at room temperature.

For working up, water is added carefully (initially dropwise with cooling!), the mixture is extracted several times using ethyl acetate, the combined organic phases are dried over sodium sulphate and concentrated in vacuo, and the residue is purified on silica gel by means of chromatography (eluent: dichloromethane/ethyl acetate =15:1).

This gives 1.1 g (12 % of theory) of methyl 3-methoxy-2-[N-methyl-N-(6-phenyl-2-pyridinyl)-amino]-acrylate of melting point 89° C.–90° C.

$^1$-NMR*): (CDCl$_3$/tetramethylsilane) δ3.30(s, 3H); 3.59 (s, 3H); 3.88 (s, 3H); 6.40 (d, 1H); 7.09 (d, 1H); 7.30–7.50 (m, 5H); 8.02 (m, 2H) ppm.

Example 2

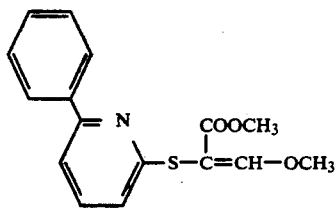

[Process (a)]

A solution of 5.2 g (0.02 mol) of methyl 2-[(6-phenyl-2-pyridinyl)-thio]-acetate in 30 ml of methyl formate is added dropwise at 5° C. to 10° C. with stirring and under an argon protective atmosphere in the course of 1 hour to a suspension of 1.32 g (0.044 mol) of sodium hydride in 30 ml of dimethylformamide, the mixture is subsequently stirred for some hours at room temperature, a pH of 6 is then established by adding saturated aqueous ammonium chloride solution, the mixture is saturated with sodium chloride and extracted several times using ethyl acetate, and the combined organic phases are dried over sodium sulphate and concentrated in vacuo.

The residue is taken up in 30 ml of dimethylformamide, 10.6 g (0.077 mol) of potassium carbonate and 2.77 g (0.022 mol) of dimethyl sulphate are added, and the mixture is stirred for 4 hours at room temperature. For working up, water is added dropwise with cooling, the mixture is extracted several times using ethyl acetate, the combined organic phases are dried over sodium sulphate and concentrated in vacuo, and the residue is purified on silica gel by means of chromatography (eluent: dichloromethane/ethyl acetate =15:1).

This gives 2.9 g (48 % of theory) of methyl 3-methoxy-2-[(6-phenyl-2-pyridinyl)-thio]-acrylate as a viscous oil.

$^1$H—NMR*): ((CDCl$_3$/tetramethylsilane)

δ=3.73 (s, 3H); 3.98 (s, 3H); 7.07 (d, 1H); 7.3–7.5 (m, 4H); 7.56 (pseudo-t, 1H); 7.98 (m, 2H); 8.02 (s, 1H) ppm The following substituted acrylic esters of the general formula (I) are obtained in a corresponding manner and following the general preparation instructions:

$$\begin{array}{c} COOR^1 \\ | \\ Py-X-C=CH-R^2 \end{array} \quad (I)$$

| Example No. | Py | R$^1$ | R$^2$ | X | Physical properties |
|---|---|---|---|---|---|
| 3 | NO$_2$-pyridinyl | CH$_3$ | OCH$_3$ | S | Fp: 67–72° C. |
| 4 | 4-chlorophenyl-pyridinyl | CH$_3$ | OCH$_3$ | >N—CH$_3$ | Fp: 120° C. |
| 5 | Br-pyridinyl | CH$_3$ | OCH$_3$ | >N—CH$_3$ | Fp: 78–79° C. |
| 6 | O$_2$N-pyridinyl | CH$_3$ | OCH$_3$ | >N—CH$_3$ | MS: 267(M⊕) 236; 190 |
| 7 | F$_3$C-, Cl-pyridinyl | CH$_3$ | OCH$_3$ | >N—CH$_3$ | $^1$H-NMR*: 3.24; 3.75; 3.80; 7.26; 7.61; 8.234 |
| 8 | Cl-pyridinyl | CH$_3$ | OCH$_3$ | S | Fp: 58–60° C. |

-continued
$$\underset{Py-X-\underset{|}{C}=CH-R^2}{COOR^1} \quad (I)$$
| Example No. | Py | R¹ | R² | X | Physical properties |
|---|---|---|---|---|---|
| 9 | 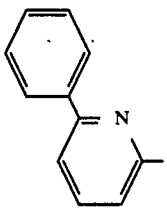 | C₂H₅ | OCH₃ | 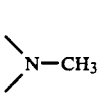 N—CH₃ | ¹H-NMR*: 1.15; 3.30; 3.85; 4.17; 6.40; 7.07; 7.3–7.5; 8.02 |
| 10 | 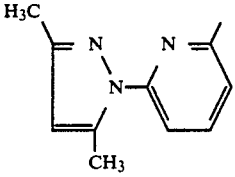 | CH₃ | OCH₃ | S | Fp: 95–96° C. |
| 11 | 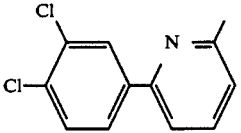 | CH₃ | OCH₃ | N—CH₃ | ¹H-NMR*: 3.74; 4.0; 7.10; 7.39; 7.49; 7.55; 7.79; 8.00; 8.09 |
| 12 | 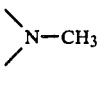 | CH₃ | OCH₃ | O | m.p: 62° C. |
| 13 | 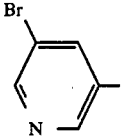 | CH₃ | OCH₃ | O | Fp: 69° C. (Z Form) |
| 14 | 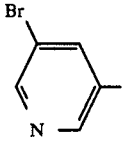 | CH₃ | OCH₃ | S | ¹H-NMR*: 3.74; 4 0; 7 10; 7 39; 7 49; 7 55; 7 79; 8 00 |
| 15 | 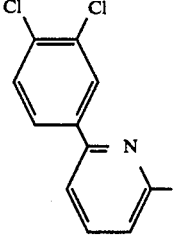 | CH₃ | OCH₃ | N—CH₃ | ¹H-NMR*: 3 26; 3 7; 3 9; 6 3–7 6 |
| 16 | 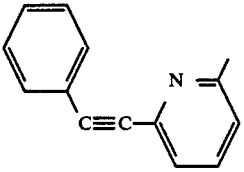 | CH₃ | OCH₃ | N—CH₃ | Fp: 100–105° C. |

-continued $$Py-X-\underset{\underset{COOR^1}{|}}{C}=CH-R^2 \quad (I)$$

| Example No. | Py | R¹ | R² | X | Physical properties |
|---|---|---|---|---|---|
| 17 | ![2-bromo-6-methylpyridine] | $CH_3$ | $N(CH_3)_2$ via $=N$ | $-N(CH_3)-$ | Fp. 107° C. |
| 18 | ![6-(4-chlorophenylethynyl)-2-methylpyridine] | $CH_3$ | $N(CH_3)_2$ via $=N$ | $-N(CH_3)-$ | Fp. 152–153° C. |
| 19 | ![3-(4-chlorophenyl)-5-methylpyridine] | $CH_3$ | $OCH_3$ | O | Fp. 62–63° C. |
| 20 | ![6-methyl-2-(4-chlorophenylethynyl)pyridine] | $CH_3$ | $OCH_3$ | $-N(CH_3)-$ | |

*The ¹H-NMR-spectra were recorded in deuterochloroform (CDCl₃) with tetramethylsilane (TMS) as the internal standard. The chemical shift is indicated as δ value in ppm.

Preparation of the starting compounds

Example IV-1

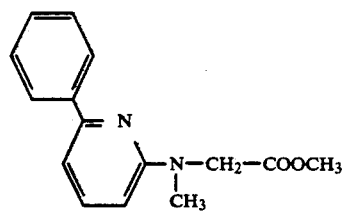

6.75 g (0.0555 mol) of phenylboronic acid, dissolved in a little methanol, are added dropwise with vigorous stirring at room temperature in the course of 30 minutes to 13 g (0.05 mol) of methyl N-(6-bromo-2-pyridinyl)-N-methylaminoacetate and 1.0 g of tetrakis(triphenylphosphine)-palladium(O) in 100 ml of benzene and 50 ml of 2-molar aqueous sodium carbonate solution, the mixture is subsequently stirred at reflux temperature until the starting material is no longer detectable in the gas chromatogram, the mixture is cooled, the organic phase is separated off, washed with water, dried over sodium sulphate and concentrated, and the residue is purified by column chromatography on silica gel (eluent: dichloromethane/n-hexane=1:1).

This gives 11.7 g (91 % of theory) of methyl N-(6-phenyl-2-pyridinyl)-N-methylamino-acetate as an oil.

¹H-NMR (CDCl₃/tetramethylsilane): δ=3.18 (s, 3H); 3.72 (s, 3H); 4.41 (s, 2H); 6.54 (d, 1H); 7.11 (d, 1H); 7.30-7.48 (m, 3H); 7.57 (dd, 1H); 7.98 (m, 2H) ppm.

Example IV-2

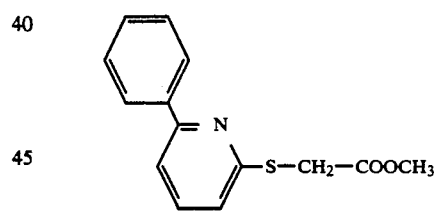

13.5 g (0.11 mol) of phenylboronic acid, dissolved in a little methanol, is added dropwise with vigorous stirring at room temperature in the course of 30 minutes to a mixture of 13.1 g (0.05 mol) of methyl 2-(6-bromo-2-pyridinylthio)-acetate and 2.5 g of tetrakis(triphenylphosphine)-palladium(0) in 200 ml of benzene and 100 ml of 2-molar aqueous sodium carbonate solution, the mixture is subsequently stirred for 15 hours at reflux temperature, the mixture is cooled, the organic phase is separated off, washed with water and dried over sodium sulphate, and the residue is purified by column chromatography on silica gel (eluent: dichloromethane/n-hexane =1:1).

This gives 10.3 g (79.4 % of theory) of methyl 2(6-phenyl-2-pyridinylthio)-acetate as an oil.

¹H-NMR*): (CDCl₃/tetramethylsilane):
δ=3.73 (s, 3H); 4.06 (s, 2H); 7.17 (d, 1H); 7.35-7.5 (m, 4H); 7.58 (t, 1H); 8.0 (m, 2H).

Example IV-3

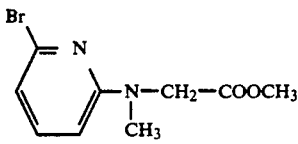

A mixture of 17 g (0.12 mol) of methyl N-methylglycinate hydrochloride, 29 g (0.12 mol) of 2,6-dibromopyridine, 27 g (0.2 mol) of potassium carbonate and 200 ml of dioxane is refluxed for 48 hours, the mixture is subsequently filtered, and the filtrate is concentrated and purified by chromatography on silica gel (eluent: dichloromethane/n-hexane = 1:1).

This gives 13.1 g (41 % of theory) of methyl N(6-bromo-2-pyridinyl)-N-methylaminoacetate of melting point 47° C.-48° C.

$^1$H-NMR*): (CDCl$_3$/tetramethylsilane):
$\delta$ = 3.10 (s, 3H); 3.75 (s, 3H); 4.35 (s, 2H); 6.46 (d, 1H); 6.75 (d, 1H); 7.31 (pseudo-t, 1H) ppm.

Example IV-4

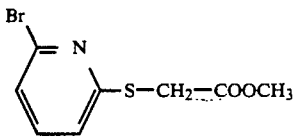

A mixture of 23.7 g (0.1 mol) of 2,6-dibromopyridine, 10.6 g (0.1 mol) of methyl thioacetate, 10 g (0.075 mol) of potassium carbonate and 100 ml of dioxane is refluxed for 20 hours with stirring under an argon protective gas atmosphere, the mixture is subsequently cooled, water is added, and the mixture is extracted using ethyl acetate, dried over sodium sulphate and concentrated in vacuo. The residue is recrystallized from diisopropyl ether/n-hexane.

This gives 19.4 g (74 % of theory) of methyl 2-(6-bromo-2-pyridinylthio)-acetate of melting point 32° C.-34° C.

Use Examples

In the Use Examples which follow, the compound mentioned below was used as the comparison substance:

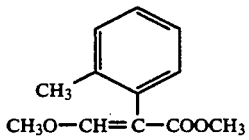
(A)

Methyl 3-methoxy-2-(2-methylphenyl)-acrylate (disclosed in EP 178,826).

Example A

| Pyricularia test (rice)/protective | |
|---|---|
| Solvent | 12.5 parts by weight of acetone |
| Emulsifier | 0.3 parts by weight of alkylaryl polyglycol ether |

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous store suspension of Pyricularia oryzae. The plants are then placed in a greenhouse at 100% relative atmospheric humidity and 25° C.

Evaluation of the disease infestation is carried out 4 days after the inoculation.

In this test, for example, the compounds of Preparation Examples 1, 2, 4, 5 and 9 show a clearly superior activity compared with the prior art.

Example B

| Leptosphaeria nodorum test (wheat)/protective | |
|---|---|
| Solvent | 100 parts by weight of dimethylformamide |
| Emulsifier | 0.25 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, for example, the compounds according to Preparation Examples 1 and 5 show a clearly superior activity compared with the prior art.

It is understood that the specification and examples are illustrative but not limitative of the present invention and that other embodiments within the spirit and scope of the invention will suggest themselves to those skilled in the art.

We claim:

1. A pyridyl-substituted acrylic ester of the formula

(I)

in which
R$^1$ represents straight-chain or branched alkyl which has 1 to 6 carbon atoms, or represents aralkyl which has 1 to 4 carbon atoms in the straight-chain or branched alkyl moiety and 6 to 10 carbon atoms in the aryl moiety and which is optionally monsubstituted to pollysubstituted in the aryl moiety by identical or different substituents from the group consisting of halogen, cyano, nitro, in each case straight-chain or branched alkyl, alkoxy or alkylthio, each having 1 to 4 carbon atoms, in each case straight-chain or branched halogenoalkyl, halogenoalkoxy or halogenoalkylthio, each having 1 to 4 carbon atoms and 1 to 9 identical or different halogen atoms, each case straight-chain or branched alkoxycarbonyl or alkoximinoalkyl, each having 1 to 8 carbon atoms in the individual alkyl moieties, cycloalkyl which has 3 to 7 carbon atoms, double-linked alkanediyl which has 3 to 5 carbon atoms, aryl, aralkyl, aryloxy or aralkyloxy, each of which has 6 to 10 carbon atoms in the aryl moiety and if appropriate 1 to 4 carbon atoms in the straight-chain or branched alkyl moiety and each of which is optionally monosubstituted to polysubstituted in the aryl moiety by identical or different substituents from the group consisting of halogen, alkyl, alkoxy, alkylthio, halogenoalkyl, halogenoalkoxy or halogenoalkylthio, each having 1 to 4 carbon atoms and if appropriate 1 to 9 identical or different halogen atoms, or heteroarylalkyl or heteroaryl, each of which has 2 to 9 carbon atoms and 1 to 4 identical or different hereto atoms in the heteroaryl moiety and if appropriate 1 to 4 carbon atoms in the straight-chain or branched alkyl moiety and each of which is optionally monosubstituted to polysubstituted in the heteroaryl moiety by identical or different substituents from the group consisting of halogen, alkyl, alkoxy, alkylthio, halogenoalkyl, halogenoalkoxy or halogenoalkylthio, each having 1 to 4 carbon atoms and if appropriate 1 to 9 identical or different halogen atoms;

$R^2$ represents dialkylamino which has 1 to 6 carbon atoms in each of the individual alkyl moieties, or represents a radical —Z—$R^3$, X represents oxygen or sulphur or represents a radical

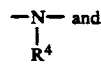

Py represents 2-pyridyl, 3-pyridyl or 4-pyridyl, each of which is monosubstituted to polysubstituted by identical or different substituents selected from the group consisting of halogen, cyano, nitro, in each case straight-chain or branched alkyl, alkoxy or alkylthio, each having 1 to 6 carbon atoms, in each case straight-chain or branched halogenoalkyl, halogenoalkoxy or halogenoalkylthio, each having 1 to 4 carbon atoms and 1 to 9 identical or different halogen atoms, in each case straight-chain or branched alkoxycarbonyl, alkoximinoalkyl, dialkylamino or dialkylaminocarbonyl, each having 1 to 4 carbon atoms in the individual alkyl moieties, in each case straight-chain or branched alkenyl or alkinyl, each having 2 to 8 carbon atoms, or aryl, aryloxy, arylthio, arylcarbonyl, aralkyl, aralkenyl, aralkinyl, aralkyloxy or heteroaryl, each of which has 6 to 10 carbon atoms in the aryl moiety and if appropriate 1 to 6 carbon atoms in the straight-chain or branched alkyl moiety or if appropriate 2 to 6 carbon atoms in the straight-chain or branched alkenyl moiety or alkinyl moiety or 2 to 9 carbon atoms and 1 to 4 identical or different hereto atoms in the heteroaryl moiety and each of which is optionally monosubstituted to polysubstituted in the respective aryl moiety or in the heteroaryl moiety by identical or different substituents from the group consisting of halogen, alkyl, alkoxy, alkylthio, halogenoalkyl, halogenoalkoxy, halogenoalkylthio, dioxyalkylene, halogensubstituted dioxyalkylene and optionally substituted phenyl; where $R^3$ represents straight-chain or branched alkyl which has 1 to 6 carbon atoms or represents aralkyl which as 1 to 4 carbon atoms in the straight-chain or branched alkyl moiety and 6 to 10 carbon atoms in the aryl moiety and which is optionally monosubstituted to pollysubstituted in the aryl moiety by identical or different substituents as set forth as possible aryl substituents in the case of $R^1$, $R^4$ represents hydrogen, or represents straight-chain or branched alkyl which has 1 to 6 carbon atoms, or represents straight-chain or branched alkanoyl which has 1 to 6 carbon atoms in the alkyl moiety, or represents aralkyl or aryl which has 1 to 6 carbon atoms in the straight-chain or branched alkyl moiety and 6 to 10 carbon atoms in the respective aryl moiety and each of which is optionally monosubstituted to polysubstituted in the respective aryl moiety by identical or different substituents as set forth as possible aryl substituents in the case of $R^1$, and Z represents oxygen or sulphur.

2. A pyridyl-substituted acrylic ester according to claim 1, in which $R^1$ represents methyl, ethyl, n- or i-propyl or n-, i-, s- or t-butyl, or represents benzyl which is optionally monosubstituted to trisubstituted by identical or different substituents from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclo-hexyl, 1,3-propanediyl or 1,4-butanediyl, or phenyl, benzyl, phenoxy or benzyloxy, each of which is optionally monosubstituted to trisubstituted in the phenyl moiety by identical or different substituents from the group consisting of fluorine, chlorine, bromine, methyl, ethyl, methoxy, ethoxy, methylthio, trifluoromethyl, difluoromethoxy, trifluoromethoxy and trifluoromethylthio, $R^2$ represents dialkylamino which has 1 to 4 carbon atoms in each of the individual alkyl moieties, or represents a radical —Z—$R^3$, X represents oxygen or sulphur or represents a radical

Py represents 2-pyridyl, 3-pyridyl or 4-pyridyl, each of which is optionally monosubstituted to trisubstituted by identical or different substituents, at least one substituent in each case representing phenyl, naphthyl, phenoxy, phenylthio, phenylcarbonyl, benzyl, phenylethyl, phenylpropyl, phenylethenyl, benzyloxy or heteroaryl, each of which is optionally monosubstituted to trisubstituted by identical or different substituents from; the series consisting of fluorine, chlorine, bromine, methyl, ethyl, n- or i-propyl, n-, i-, s- or t-butyl, methoxy, ethoxy, n- or i-propoxy, methylthio, ethylthio, trifluoromethyl, trifluoromethoxy, trifluoromethylthio, dioxymethylene, or by phenyl which is optionally monosubstituted to trisubstituted by identical or different substituents from the group consisting of fluorine, chlorine, methyl, methoxy or trifluoromethyl, the heteroaryl radicals being selected from the group consisting of

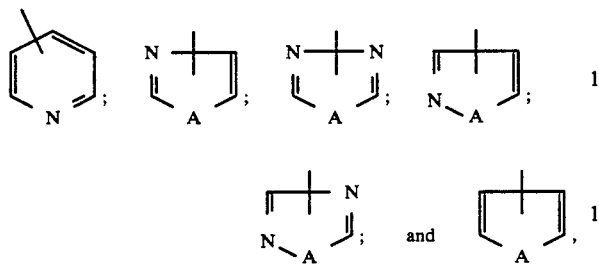

which can also be benzo-fused,
in which
A in each case represents oxygen or sulphur or represents an NH group: other possible pyridyl substituents being selected from the group consisting of fluorine, chlorine, bromine, cyano, nitro, methyl, ethyl, n- or i- propyl, n-, i-, s- or t-butyl, methoxy, ethoxy, n- or i-propoxy, nethylthio,trifluoromethyl,trifluoromethoxy,trifluoromethylthio,methoxycarbonyl, ethoxycarbonyl,methoximinomethyl,ethoxlminomethyl, methoximinoethyl, ethoximinoethyl, dimethylamino, diethylamino, dimethylcarbamoyl, diethylcarbamoyl, allyl, butenyl and propargyl;
where
$R^3$ represents methyl, ethyl, n- or i-propyl, or n-, i-, s- or t-butyl, or represents benzyl which is optionally monosubstituted to trisubstituted by identical or different substituents, as mentioned in the case of $R^1$ and $R^2$;
$R^4$ represents hydrogen, methyl, ethyl, n- or i-propyl or n-, i-, s- or t-butyl, or represents acetyl, propionyl or n- or i-butyryl or represents benzyl or phenyl, each of which is optionally monosubstituted to trisubstituted by identical or different substituents as mentioned in the case of $R^1$ and $R^2$, and
Z represents oxygen or sulphur.

3. A pyridyl-substituted acrylic ester according to claim 1,
in which
$R^1$ represents methyl or ethyl,
$R^2$ represents methoxy or ethoxy,
X represents oxygen or sulphur or represents a radical

Py represents 2-pyridyl, 3-pyridyl or 4-pyridyl, each of which is optionally monosubstituted to trisubstituted by identical or different substituents, at least one substituent in each case representing benzofused phenyl, phenoxy, phenylcarbonyl, benzyl, pyridyl, pyrazolyl, oxazolyl, thiazolyl, thienyl, furyl, thiadiazolyl, oxadiazolyl, imidazolyl or triazolyl, each of which is optionally monosubstituted to trisubstituted by identical or different substituents from the group consisting of fluorine, chlorine, methyl, ethyl, methoxy, trifluoromethyl, dioxymethylene and phenyl, other possible pyridyl substituents in each case being selected from the group consisting of fluorine, chlorine, bromine, cyano, nitro, methyl, ethyl, methoxy, methylthio, trifluoromethyl, trifluoromethylthio, methoxycarbonyl, ethoxycarbonyl and dimethylamino, and
$R^4$ represents methyl, ethyl or benzyl.

4. A compound according to claim 1, wherein such compound is methyl 3-methoxy-2[N-methyl-N-(6-phenyl2-pyridinyl)-amino]-acrylate of the formula

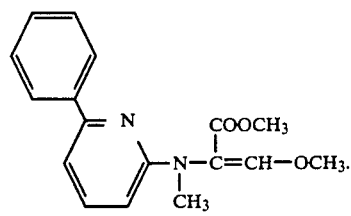

5. A compound according to claim 1, wherein such compound is methyl 3-methoxy-2[(6-phenyl2-pyridinyl)-thio]-acrylate of the formula

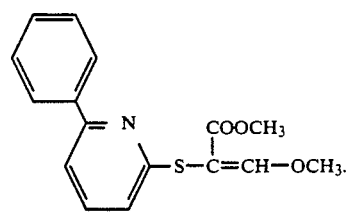

6. A compound according to claim 1, wherein such compound is methyl 3-methoxy-2[N-methyl-N-(6-(4-chlorophenyl2-pyridinyl}-amino]-acrylate of the formula

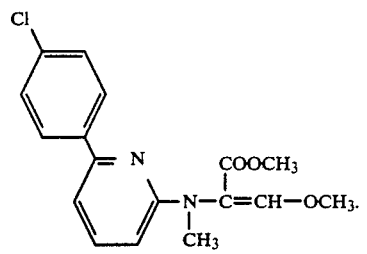

7. A compound according to claim 1, wherein such compound is methyl 3-methoxy-2[N-methyl-N-(6-bromo-2-pyridinyl)-amino]-acrylate of the formula

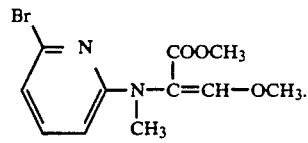

8. A compound according to claim 1, wherein such compound is methyl 3-methoxy-2[N-methyl-N-{6-(3,4-dichlorophenyl)-2-pyridinyl}-amino]-acrylate of the formula

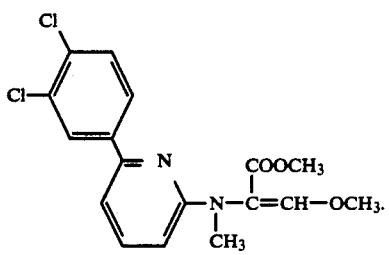

9. A compound according to claim 1, wherein such compound is methyl 3-methoxy-2[N-methyl-N-(6-phenylethenyl-2-pyridinyl)-amino]-acrylate of the formula

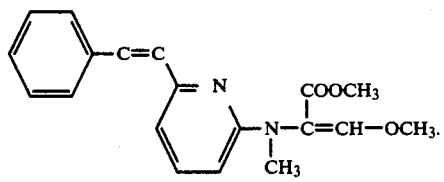

10. A compound according to claim 1, wherein such compound is methyl 3-methoxy-2-[N-methyl-N-{6-(3,4-dimethylphenyl)-2-pyridinyl}-amino]-acrylate of the

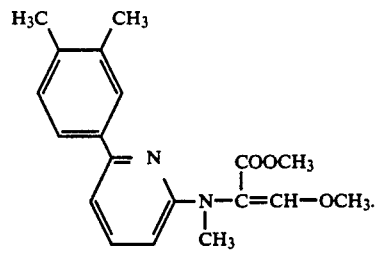

11. A fungicidal composition comprising a fungicidally effective amount of a compound according to claim 1 and a diluent.

12. A method of combating fungi which comprises applying to such fungi or to a fungus habitat a fungicidally effective amount of a compound according to claim 1.

13. The method according to claim 12, wherein such compound is
   methyl 3-methoxy-2-[N-methyl-N-(6-phenyl-2-pyridinyl)-amino]-acrylate,
   methyl 3-methoxy-2-[(6-phenyl-2-pyridinyl)-thio]-acrylate,
   methyl 3-methoxy-2-[N-methyl-N-{6-(4-chlorophenyl)-2-pyridinyl}-amino]-acrylate,
   methyl 3-methoxy-2-(N-methyl-N-(6-bromo-2-pyridinyl)-amino]-acrylate,
   methyl 3-methoxy-2-[N-methyl-N-{(6-(3,4-dichlorophenyl)-2-pyridinyl}-amino]-acrylate,
   methyl 3-methoxy-2-[N-methyl-N-(6-phenylethenyl-2-pyridinyl)-amino]-acrylate or
   methyl 3-methoxy-2-[N-methyl-N-{6(3,4dimethylphenyl-2-pyridinyl}-amino]-acrylate,

* * * * *

UNITED STATES PATENT AND TRADEMARK OFFICE
CERTIFICATE OF CORRECTION

PATENT NO. : 5,008,275

DATED : April 16, 1991

INVENTOR(S) : Klausener et al.

It is certified that error appears in the above-identified patent and that said Letters Patent is hereby corrected as shown below:

Col. 40, lines 4-5   After " trifluoromethyl " insert -- trifluoromethoxy --

Signed and Sealed this

Thirteenth Day of April, 1993

Attest:

STEPHEN G. KUNIN

*Attesting Officer*   Acting Commissioner of Patents and Trademarks